US010207846B2

(12) United States Patent
Loritz

(10) Patent No.: US 10,207,846 B2
(45) Date of Patent: Feb. 19, 2019

(54) PACKAGE WITH LUER FITTING STORAGE INSERT

(71) Applicant: Kenneth Anthony Loritz, Irvine, CA (US)

(72) Inventor: Kenneth Anthony Loritz, Irvine, CA (US)

( * ) Notice: Subject to any disclaimer, the term of this patent is extended or adjusted under 35 U.S.C. 154(b) by 129 days.

(21) Appl. No.: 15/119,092

(22) PCT Filed: Feb. 13, 2015

(86) PCT No.: PCT/US2015/015863
§ 371 (c)(1),
(2) Date: Aug. 15, 2016

(87) PCT Pub. No.: WO2015/123546
PCT Pub. Date: Aug. 20, 2015

(65) Prior Publication Data
US 2017/0050779 A1 Feb. 23, 2017

Related U.S. Application Data

(60) Provisional application No. 61/939,573, filed on Feb. 13, 2014.

(51) Int. Cl.
B65D 51/00 (2006.01)
A61J 1/14 (2006.01)
A61J 1/05 (2006.01)
A24F 47/00 (2006.01)
A61M 5/00 (2006.01)
B65D 41/04 (2006.01)

(52) U.S. Cl.
CPC .......... B65D 51/002 (2013.01); A24F 47/008 (2013.01); A61J 1/05 (2013.01); A61J 1/14 (2013.01); A61M 5/002 (2013.01); B65D 41/04 (2013.01)

(58) Field of Classification Search
CPC ..... B65D 51/002; B65D 41/04; A24F 47/008; A61M 5/002; A61J 1/05; A61J 1/14
USPC .................................. 215/247, 249; 604/415
See application file for complete search history.

(56) References Cited

U.S. PATENT DOCUMENTS

| 2,911,123 | A | 11/1959 | Saccomanno |
| 3,047,178 | A | 7/1962 | Poitras et al. |
| 3,313,439 | A | 4/1967 | Robinson |
| 3,940,003 | A | 2/1976 | Larson |

(Continued)

OTHER PUBLICATIONS

PCT/US2015/015863, International Search Report and Written Opinion, dated May 15, 2015.

Primary Examiner — James N Smalley
(74) Attorney, Agent, or Firm — Fay Sharpe LLP

(57) ABSTRACT

An insert is disclosed for use with a container having an end wall, and sidewall that together form an internal cavity, and an opening opposite the end wall that communicates with the internal cavity. The insert includes a body having first and second ends spaced apart along a first axis. A portion of the body is dimensioned for receipt in the opening of the container. A passage extends through the body from the first end to the second end for communicating with the internal cavity of the container. An elongated recess extends inwardly from the first end of the body and is sealed from the cavity of the container.

39 Claims, 13 Drawing Sheets

(56) References Cited

U.S. PATENT DOCUMENTS

| | | | |
|---|---|---|---|
| 4,230,231 A | * | 10/1980 | Burnett .............. B65D 39/0047 |
| | | | 215/277 |
| 5,036,992 A | | 8/1991 | Mouchawar et al. |
| 5,060,812 A | * | 10/1991 | Ogle, II ............... B65D 51/002 |
| | | | 215/247 |
| 5,429,256 A | | 7/1995 | Kestenbaum |
| RE35,167 E | | 3/1996 | Mouchawar et al. |
| 5,871,110 A | | 2/1999 | Grimard et al. |
| 5,895,383 A | | 4/1999 | Niedospial, Jr. |
| 6,202,843 B1 | | 3/2001 | Kelson et al. |
| 6,666,852 B2 | | 12/2003 | Niedospial, Jr. |
| 6,997,917 B2 | | 2/2006 | Niedospial, Jr. et al. |
| 8,122,922 B2 | | 2/2012 | Baker |
| 8,512,307 B2 | | 8/2013 | Fangrow |
| 8,905,994 B1 | | 12/2014 | Lev et al. |
| 2005/0155901 A1 | | 7/2005 | Krueger et al. |

* cited by examiner

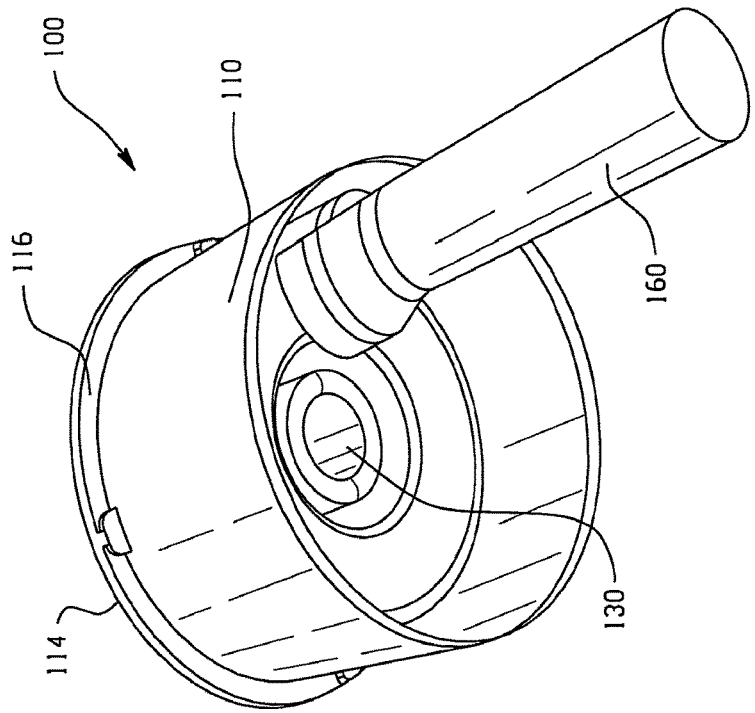
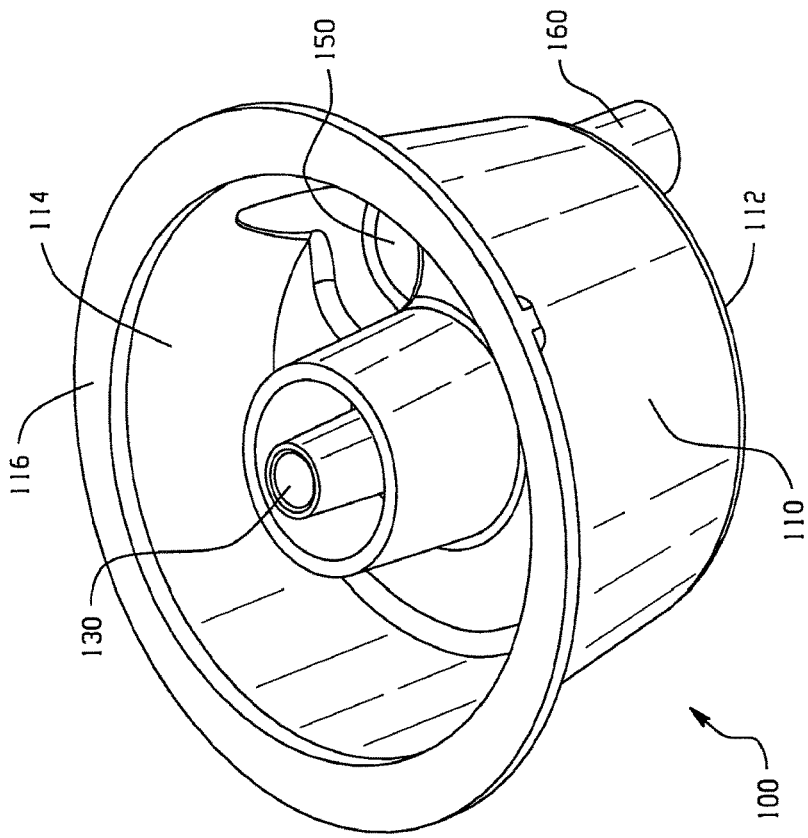

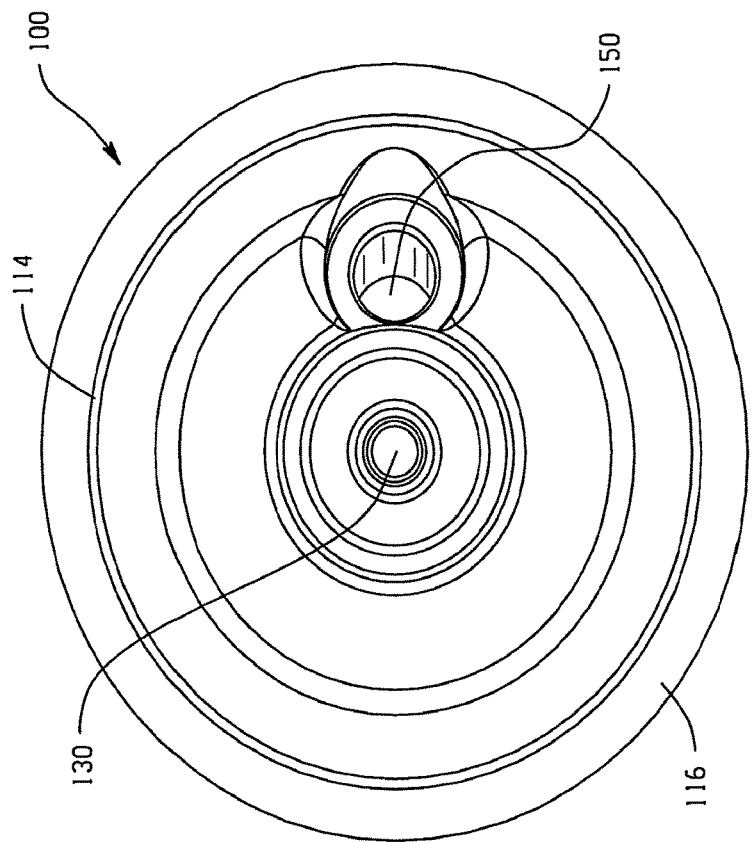
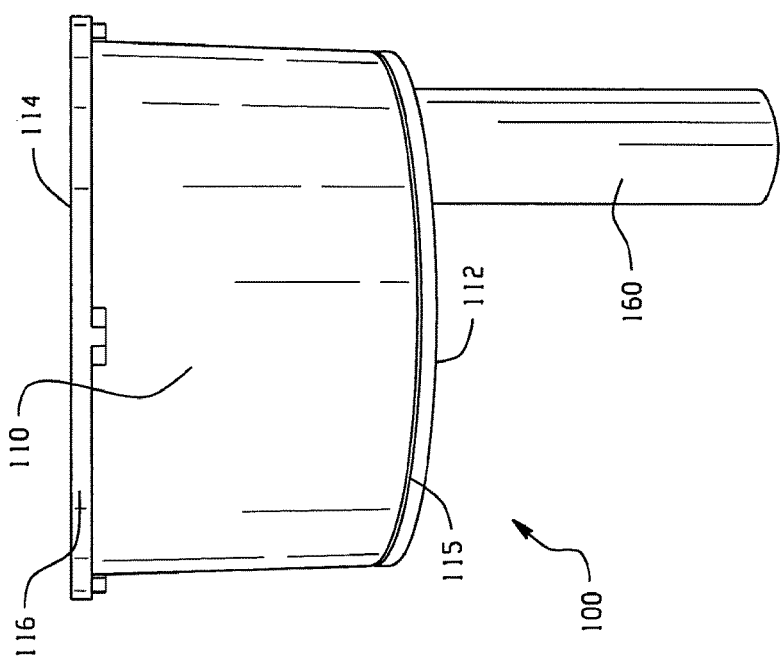

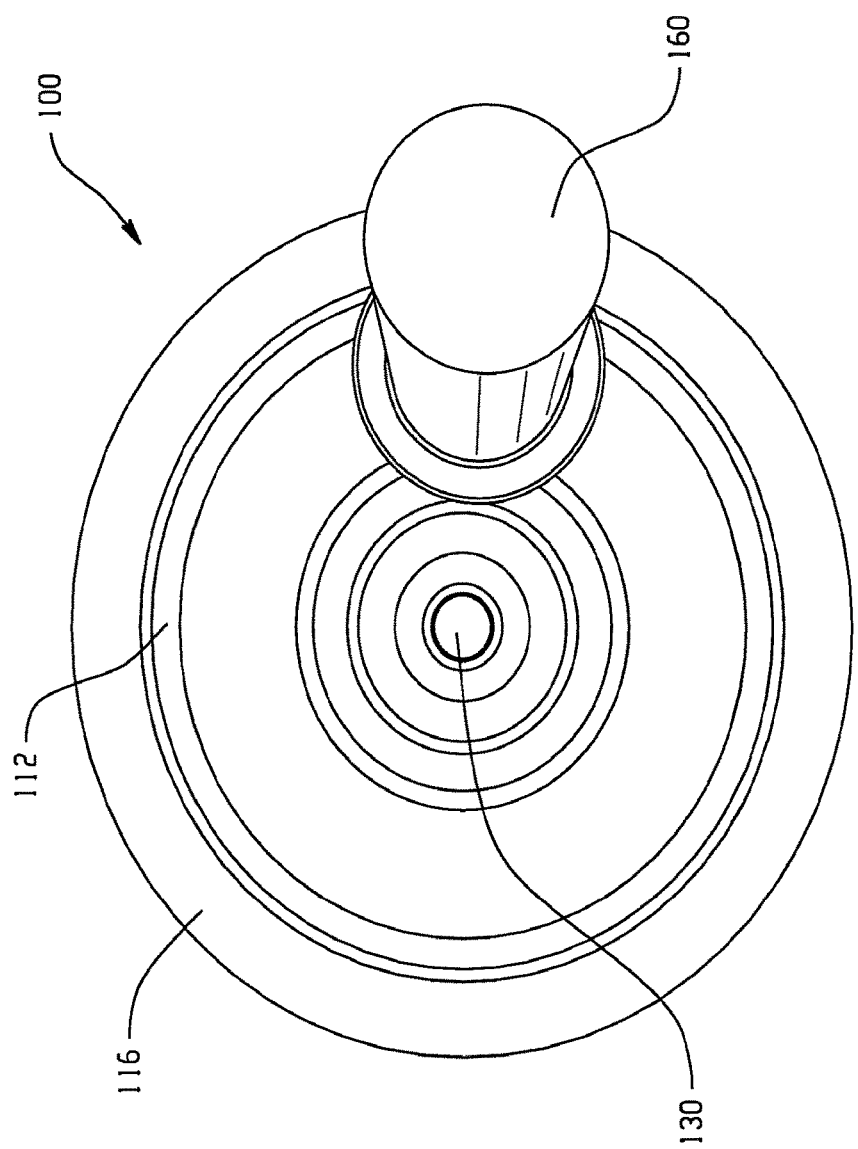

PACKAGE WITH LUER FITTING STORAGE INSERT

This application claims the priority benefit of U.S. provisional application Ser. No. 61/939,573, filed Feb. 13, 2014.

BACKGROUND

The present disclosure relates to packaging, and particularly packaging that includes an integrated storage compartment. It finds particular application as an insert to a fluid package and the insert aids in the packaging, shipping, storage, and dispensing of liquids, and will be described with particular reference thereto. For example, one use of the insert is in association with e-cigarettes while another intended use is in the medical industry. In each instance, the insert includes a storage compartment for a Luer fitting. However, it is to be appreciated that the present disclosure is also amenable to other like applications that encounter similar problems.

E-cigarettes are a recent phenomenon and are finding a wide range of use as an alternative to conventional cigarette smoking. It is estimated that approximately 10% of the smoking population has switched to e-cigarettes. An e-cigarette is designed to resemble and be used in a manner akin to a conventional cigarette, that is, a user inhales a vaporized liquid from one end of the e-cigarette and the vapor is subsequently exhaled by the user. The liquid or liquid solution (also known as e-juice or e-liquid) is vaporized by a heating element or coil that is battery-operated. The heating element vaporizes the liquid stored in an adjacent sponge, cotton, or wick material that forms a fluid reservoir or fluid storage region in the e-cigarette.

Over time, the supply of the liquid is used up. If the e-cigarette is not entirely discarded (as is common with some models of e-cigarettes), many users will refill the sponge or wick material with a new supply of e-liquid. The e-liquid has the general consistency of a syrup. To prevent damage to the heating element, it is desirable to introduce the e-liquid along an interior sidewall of an inner cavity of the e-cigarette. For example, a blunt end of a fluid dropper is positioned along the sidewall and the dropper bottle is squeezed to inject and refill the e-cigarette. In other instances, a syringe is used and the needle from a Luer fitting that is secured to the syringe is carefully positioned along the interior sidewall and a syringe plunger depressed to expel the e-liquid into the fluid storage region of the e-cigarette.

As would be appreciated, because the e-liquid is typically a sticky substance, it is common to remove the needle or Luer fitting from an end of the syringe barrel and separately store the needle. For example, an e-cigarette user often places the needle in a separate sealed plastic bag or the like so that the needle does not inadvertently become contaminated.

As also noted above, in other instances the e-cigarette may be entirely discarded. However, use of a lithium-ion battery, a tungsten heating coil, cotton or other storage material, glass, etc. that are all incorporated in a typical e-cigarette would tend to encourage use of a refillable e-cigarette.

Consequently, a need exists for a package arrangement that can be easily attached to a fluid storage container or bottle, is adapted to engage one end of the syringe during withdrawal of the fluid from the container, and also provides the additional feature of accommodating the Luer fitting/needle for storage in the container without interfering with the flow withdrawal function. It would be preferable to protect the Luer fitting/needle from contamination, and yet still be readily accessible for subsequent attachment to the end of the syringe after the syringe has been refilled with the fluid.

In still other uses (e-cigarette, medical, etc.), the modification must be easily adapted or conform to existing packaging. Another concern is whether the modification to the packaging can be preferably formed of a material that can be recycled along with remainder of the container, bottle, or package.

BRIEF DESCRIPTION

An insert is dimensioned for receipt in an associated container where the associated container has an end wall and sidewall that together form an internal cavity and an opening opposite the end wall that communicates with the internal cavity. The insert includes a body having first and second ends spaced apart along a first axis. At least a portion of the body is dimensioned for receipt in the opening of the associated container. A passage extends through the body from the first end to the second end for communicating with the internal cavity of the associated container. In addition, an elongated recess extends inwardly from the second end of the body and is sealed from the cavity of the associated container.

The recess projects in a direction substantially parallel with the first axis from second end of the body and the recess is dimensioned to extend into the cavity of the associated container.

The passage in the body has an outer, second end sized to mate with a neck of a syringe.

The elongated recess has a length measured along the first axis that is dimensioned to receive a needle/fitting therein.

The body has a shoulder adjacent the second end that is dimensioned to preclude receipt in the opening of the associated container.

The body terminates in a shoulder that is located at the second end of the body.

The recess is a closed bore.

The passage is generally centrally located in the body and the recess is offset from the passage.

The recess and the passage extend in substantially parallel relation.

The body has a substantially cylindrical outer circumferential wall that is dimensioned for sliding, sealing receipt at least partially through the opening and into a corresponding substantially cylindrically shaped cavity of the associated container.

The shoulder is substantially circumferentially continuous for engaging an end of the associated container around the opening.

The insert is a molded plastic, and preferably a polypropylene.

A seal member is interposed between the insert and the container, preferably located in a perimeter/circumferential recess at a first, lower end of the insert body that is received in the container.

A container assembly includes a container having an end wall at a first, lower end, a sidewall having a first end extending from the end wall whereby the end wall and sidewall together form an internal cavity, and an opening at a second end of the sidewall opposite the end wall (i.e., at a second, upper end of the container) that communicates with the internal cavity. A cap is selectively received at the second end of the sidewall and dimensioned for closing receipt with the opening. An insert includes a body having first and second ends spaced apart along a first axis, a portion of the body (e.g., a first end) dimensioned for receipt in the opening of the container. A passage extends through the body from the first end to the second end for communicating with the internal cavity of the container, and an elongated recess extends inwardly from the second end of the body and is sealed from the cavity of the container.

BRIEF DESCRIPTION OF THE DRAWINGS

FIGS. 13-17 are different views of the insert (top and bottom perspective views, side, top and bottom, respectively).

DETAILED DESCRIPTION

Figure 1:
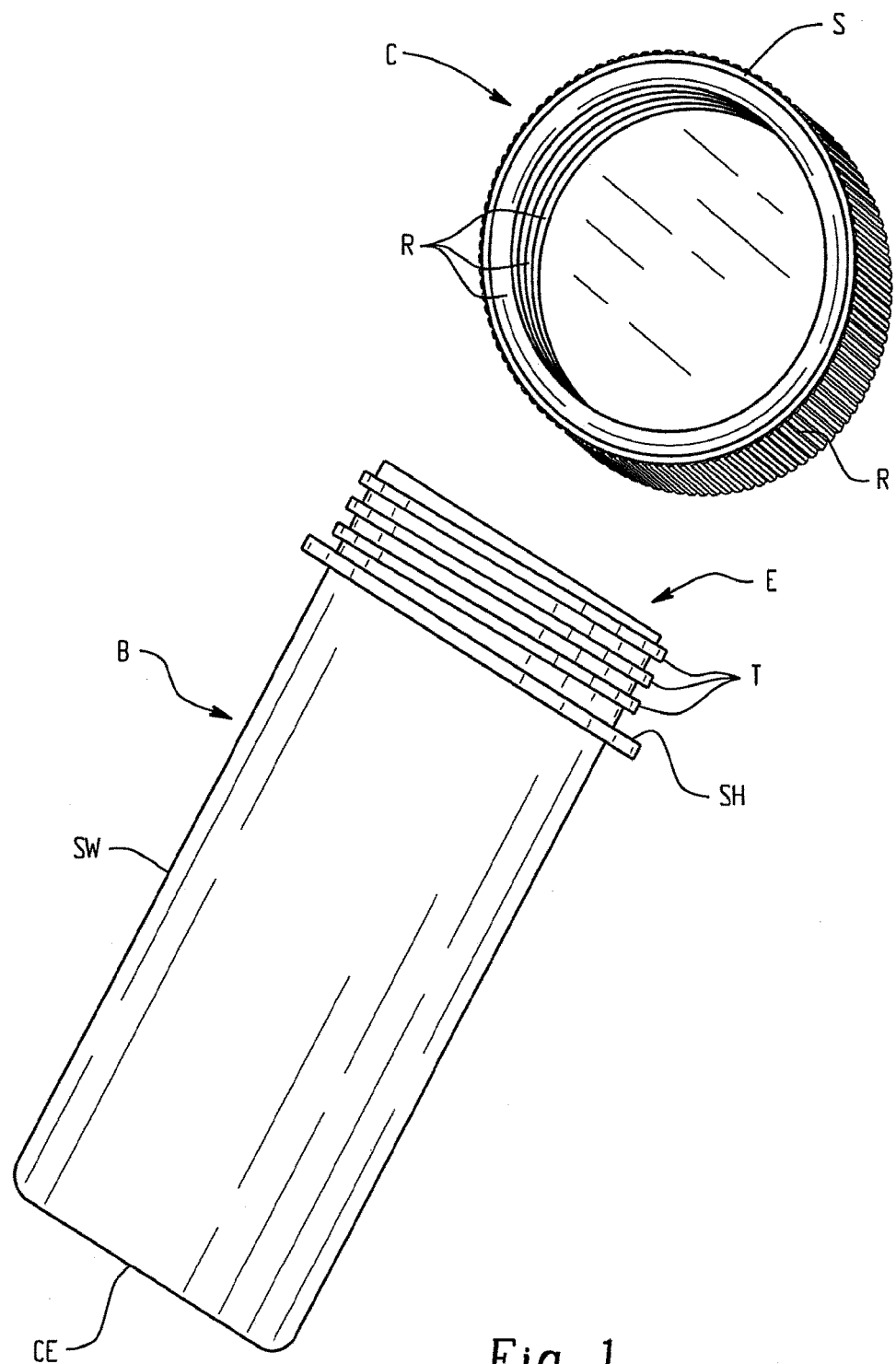
FIG. 1 is a perspective view of a conventional container assembly with a cap removed from the container.

A known container, jar, or bottle B has a generally cylindrical shape, that is the sidewall SW of the container has the shape of a hollow cylinder that is closed at a first end CE and open at a second end E as shown in FIG. 1. A cap or closure C seals the container B over the open, second end E of the container B, namely the cap C has an internal thread or thread lugs T that cooperate with corresponding external threads or thread lugs T on the container B adjacent the end E of the container. A sidewall S of the cap C abuts against a shoulder SH on the container B when the cap is fully threaded or received on the open end E of the container. The cap C may include raised ribs R in circumferentially spaced relation along an external surface to aid in gripping of the cap by a user, and facilitate rotating the cap on and off the container B.

Generally, the container B with the threaded cap C is a well-known structure and may come in a variety of sizes, for example, 10, 15, and 30 ml containers are commonly used, and can be used in a wide variety of industries, e.g., food products, medical and dental, pharmaceutical, laboratories, cosmetics, arts and crafts, hobbies, household storage, fishing and outdoor sports, grease and lubricants, manufacturing, hardware and storage, automotive, or novelties, although one skilled in the art will appreciate that this list is exemplary only and not deemed to be limiting or exhaustive. It is common for containers B of this type to be an injection molded plastic construction, and one commonly used material is a polypropylene such as metallocene polypropylene, which is derived from natural gas. Again, however, still other plastics may be used to manufacture the container, cap, etc. For example, it would be desirable that all components of the container, etc. be made from a material that can be easily recycled such as a polypropylene, although other materials can be suitably used without departing from the scope and intent of the present disclosure.

Figure 2:
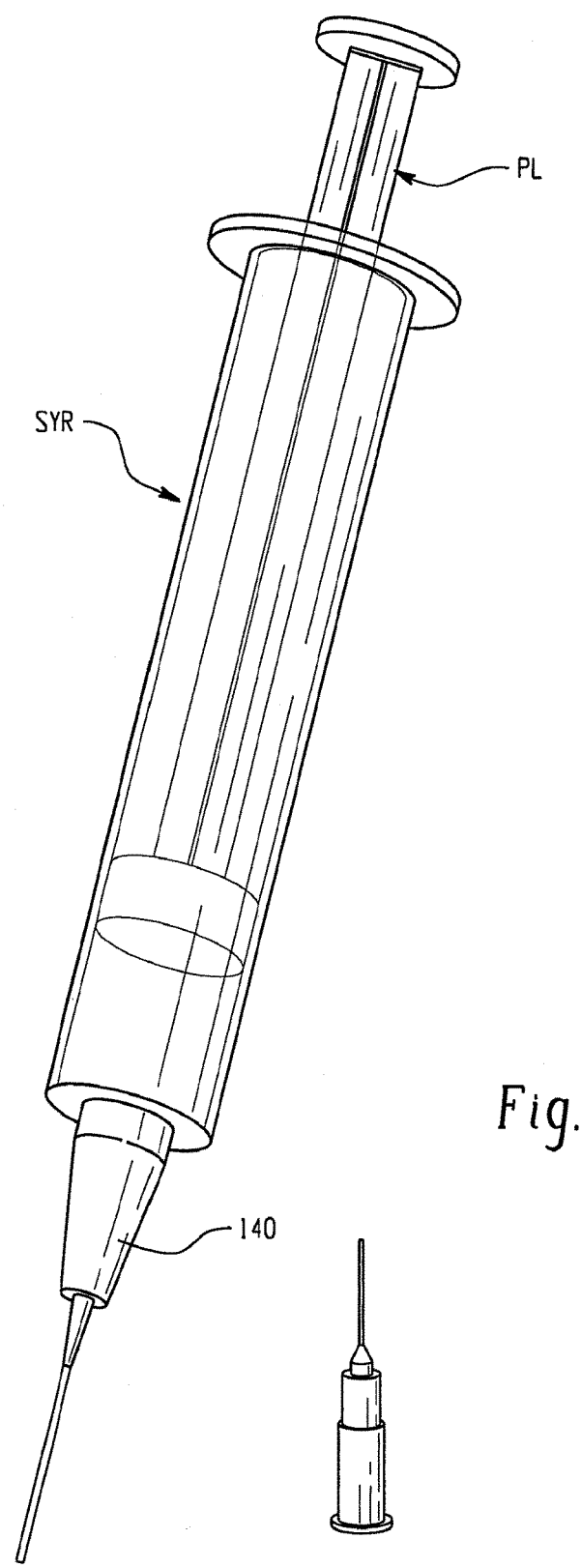
FIG. 2 is a perspective view of a conventional syringe.
Figure 3:
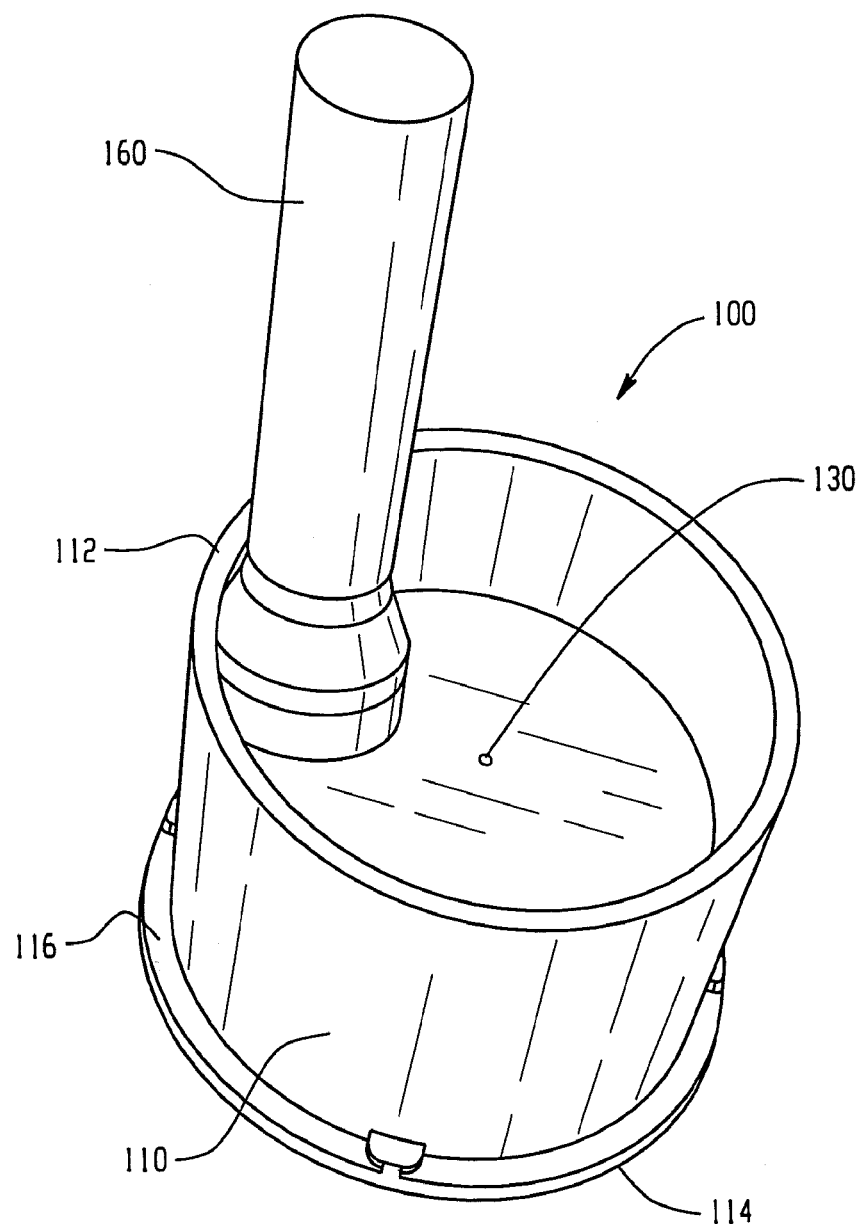
FIG. 3 is a perspective view of a subject new insert formed in accordance with the present disclosure.
Figure 4:
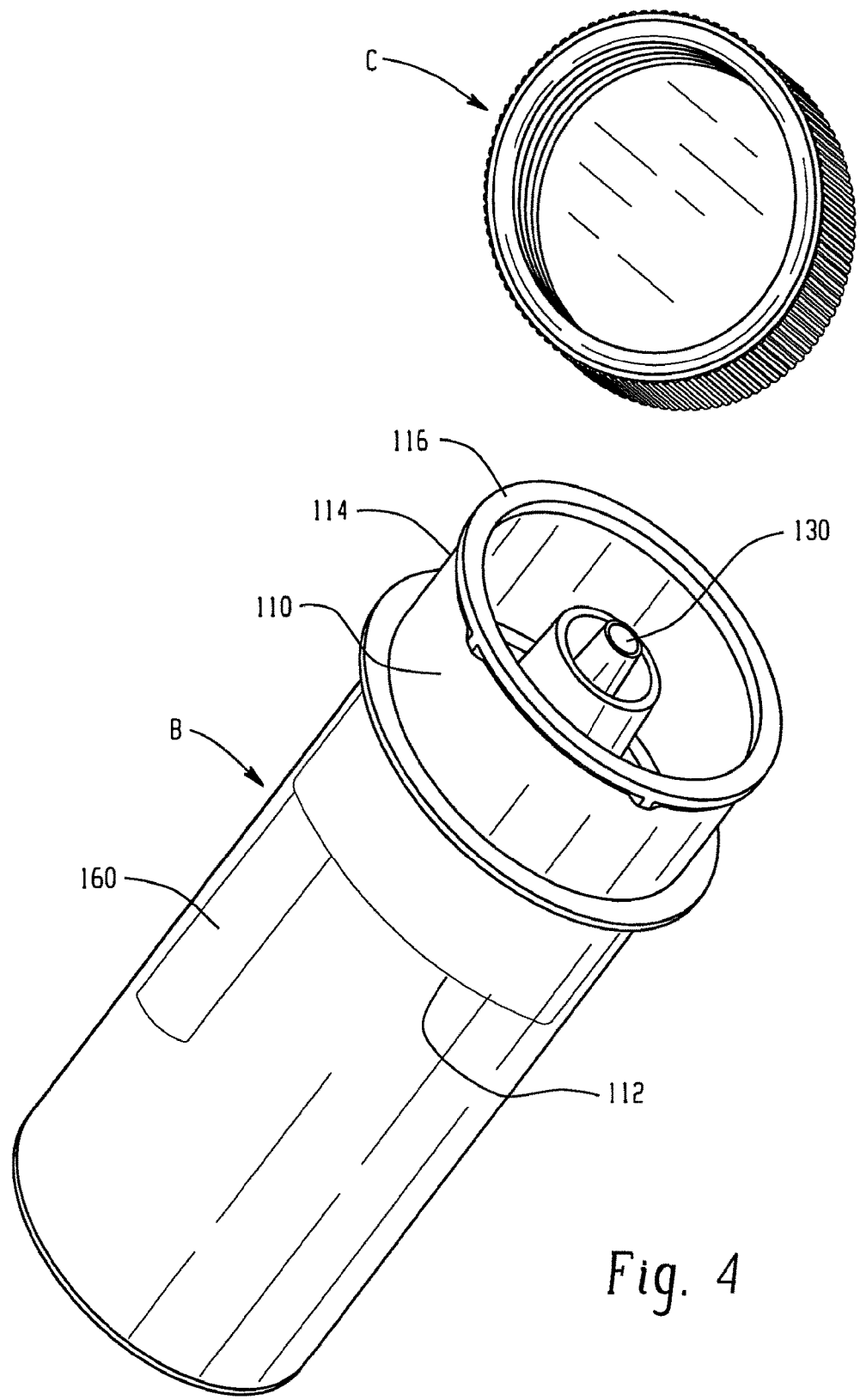
FIG. 4 is a perspective view of the insert received into an open end of a container, where the cap is removed from the container.
Figure 5:
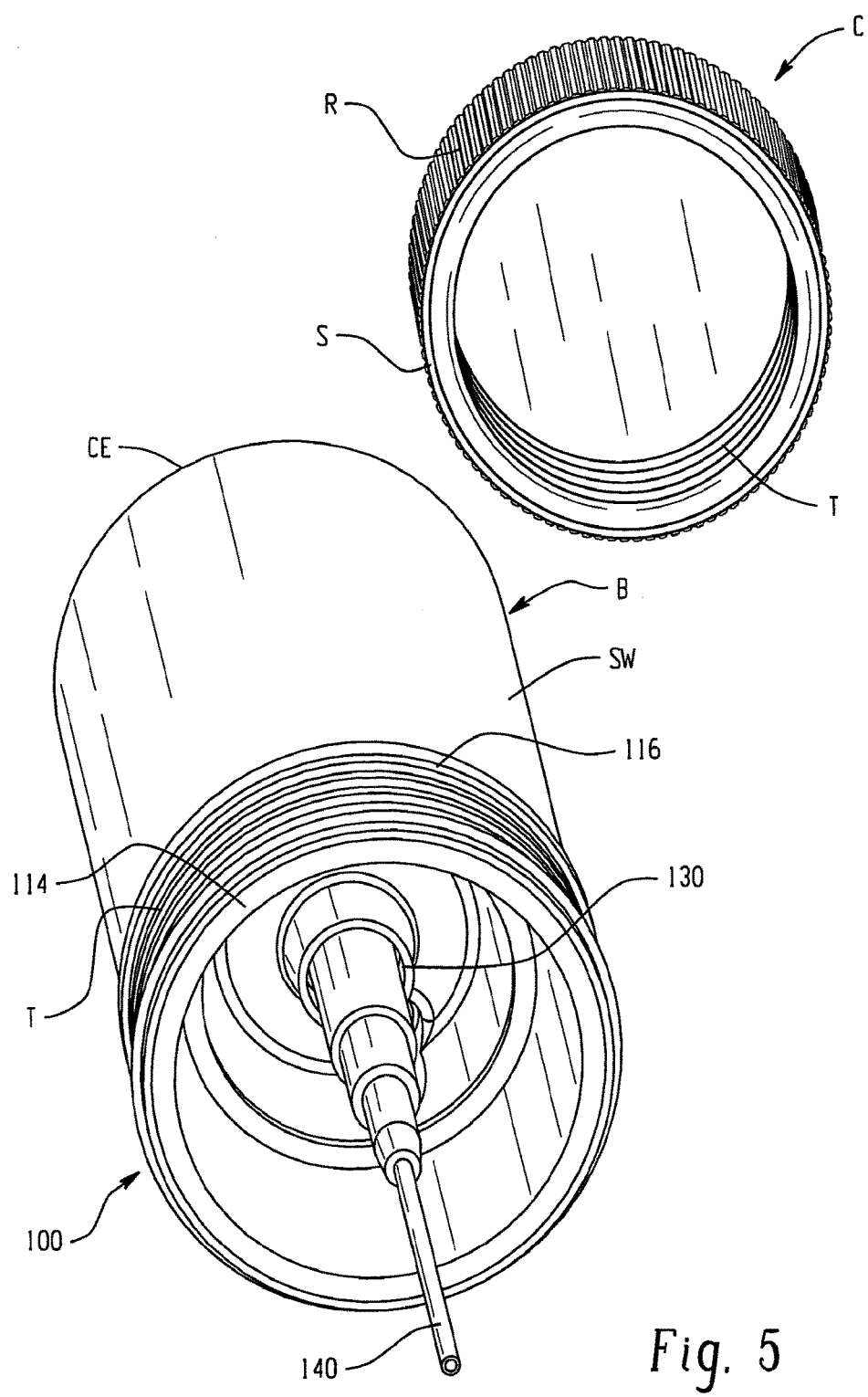
FIG. 5 is a view of the insert received in the container and with a connection or fitting received in the insert.
Figure 6:
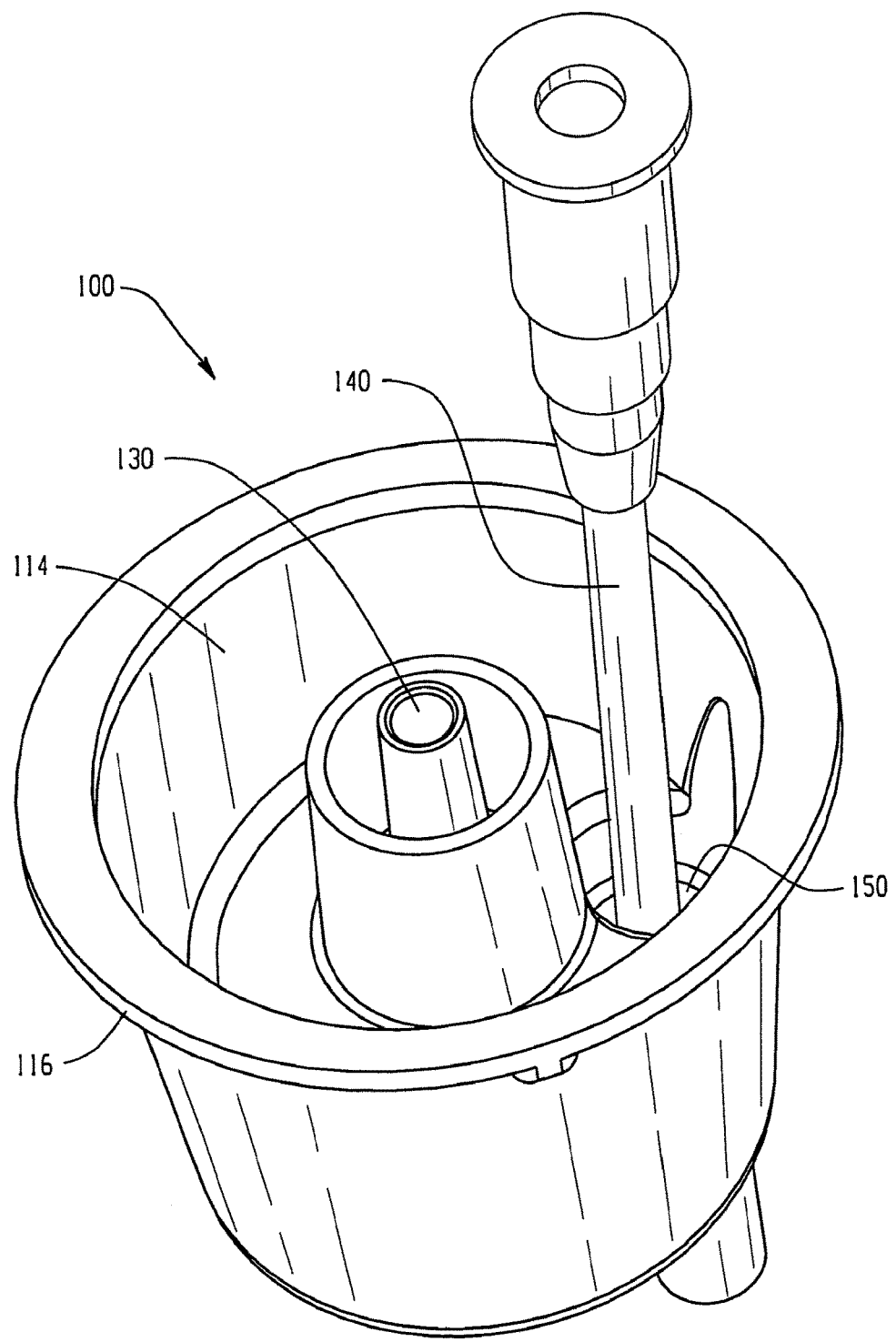
FIG. 6 shows the fitting or connection received in a storage recess or cavity of the insert.
Figure 7:
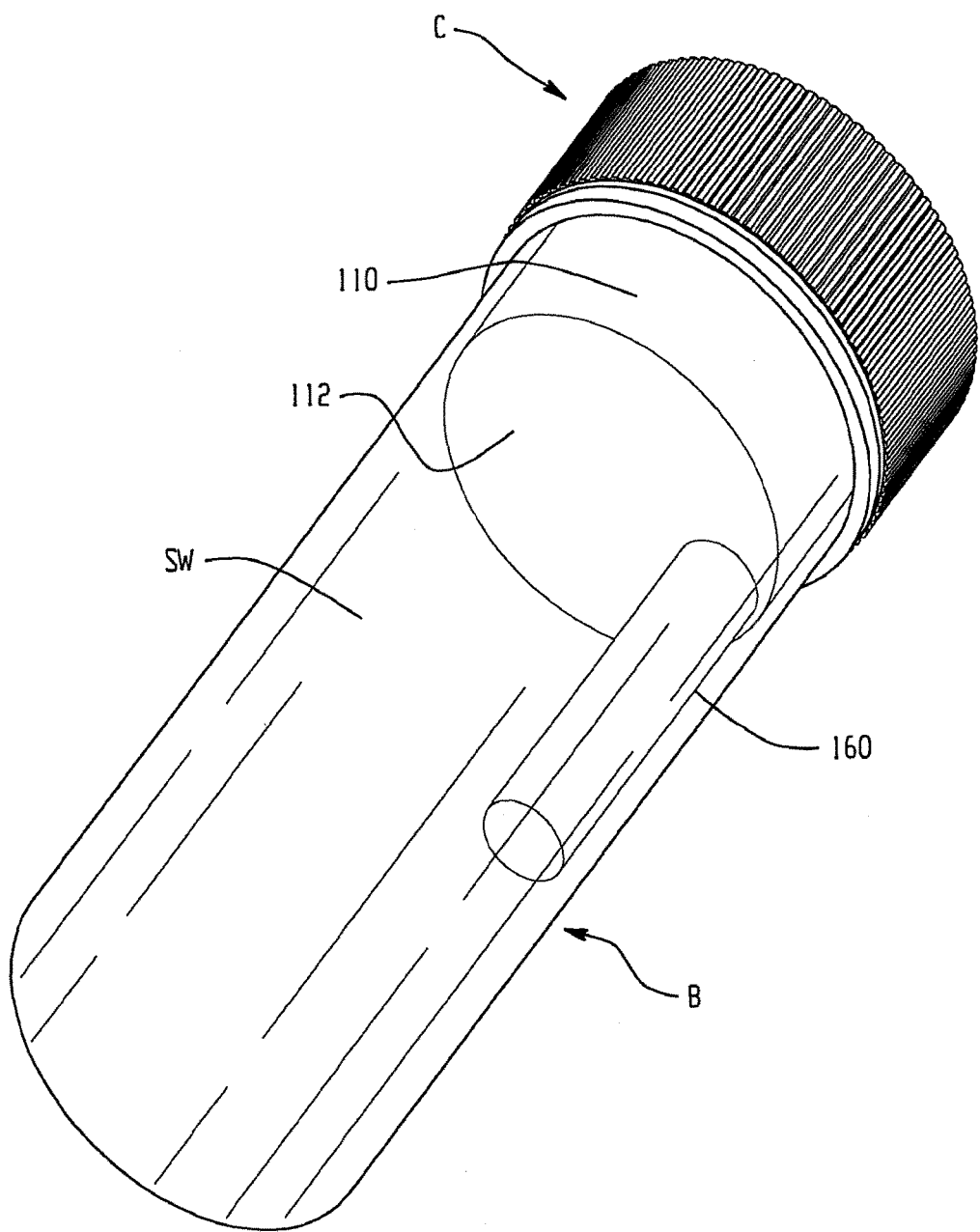
FIG. 7 shows the cap received on the container with the insert inside the container.
Figure 8:
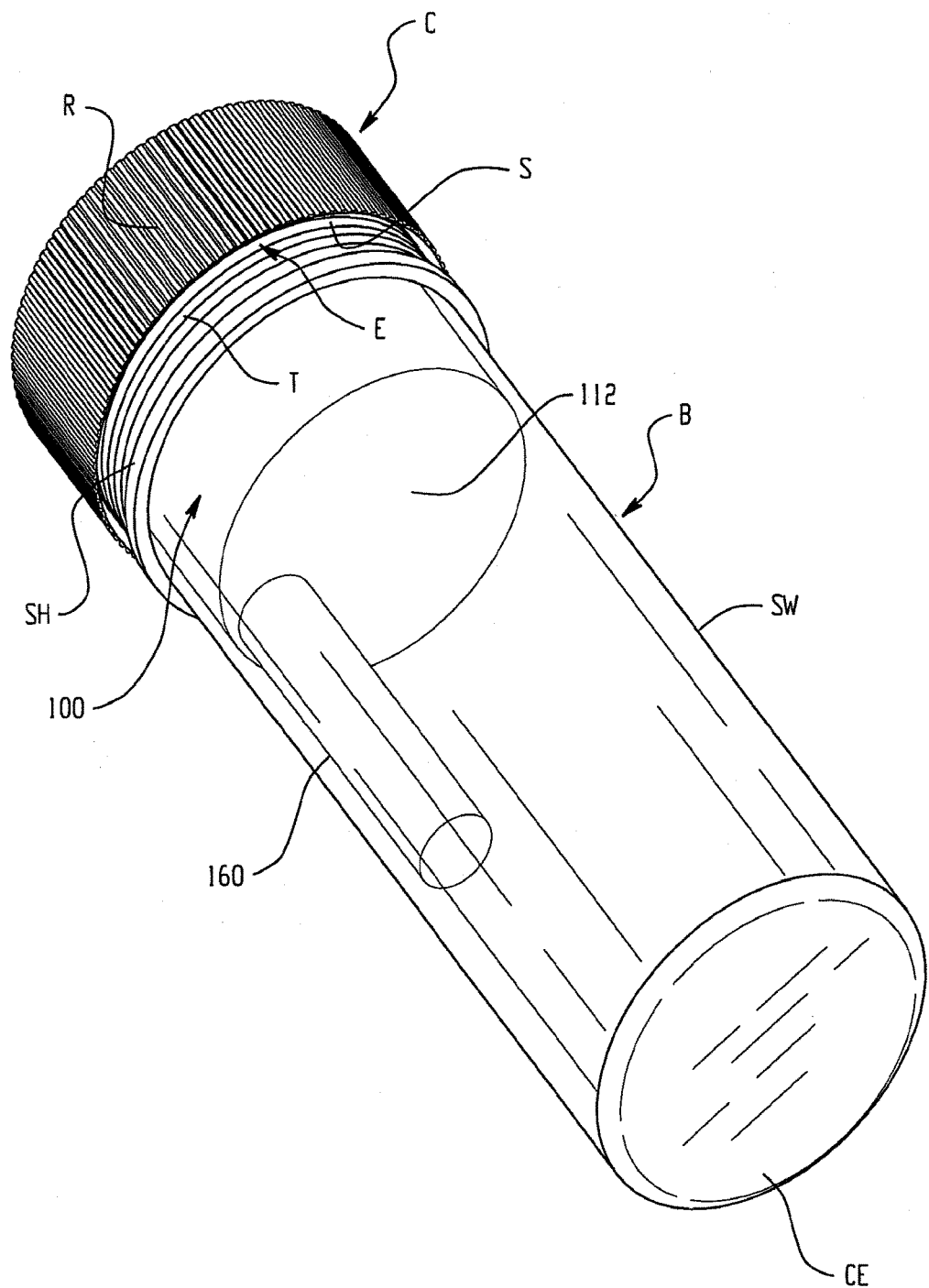
FIG. 8 is a view similar to FIG. 7.
Figure 10:
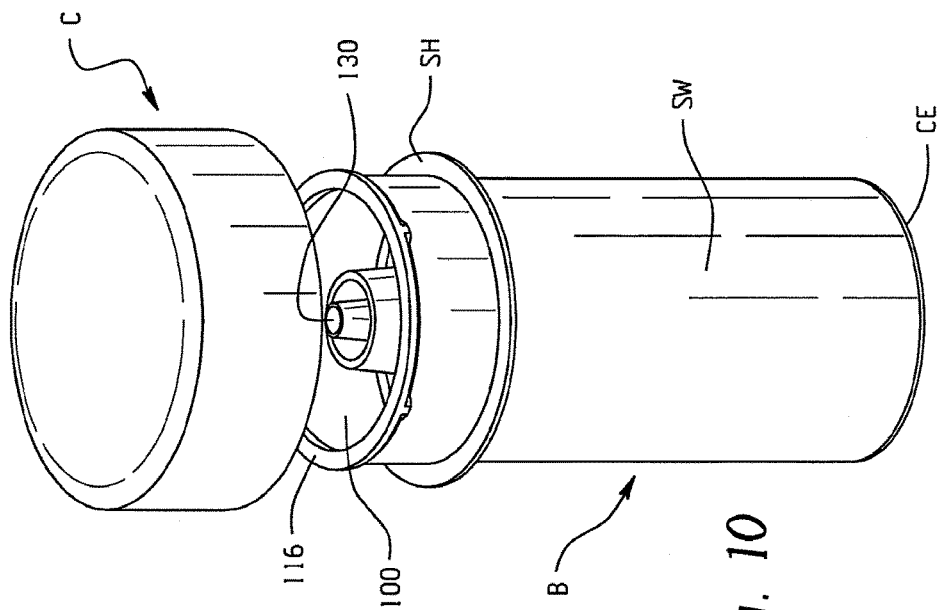
FIGS. 9-12 are different views of the container assembly, the cap omitted from FIG. 12.
Figure 9:
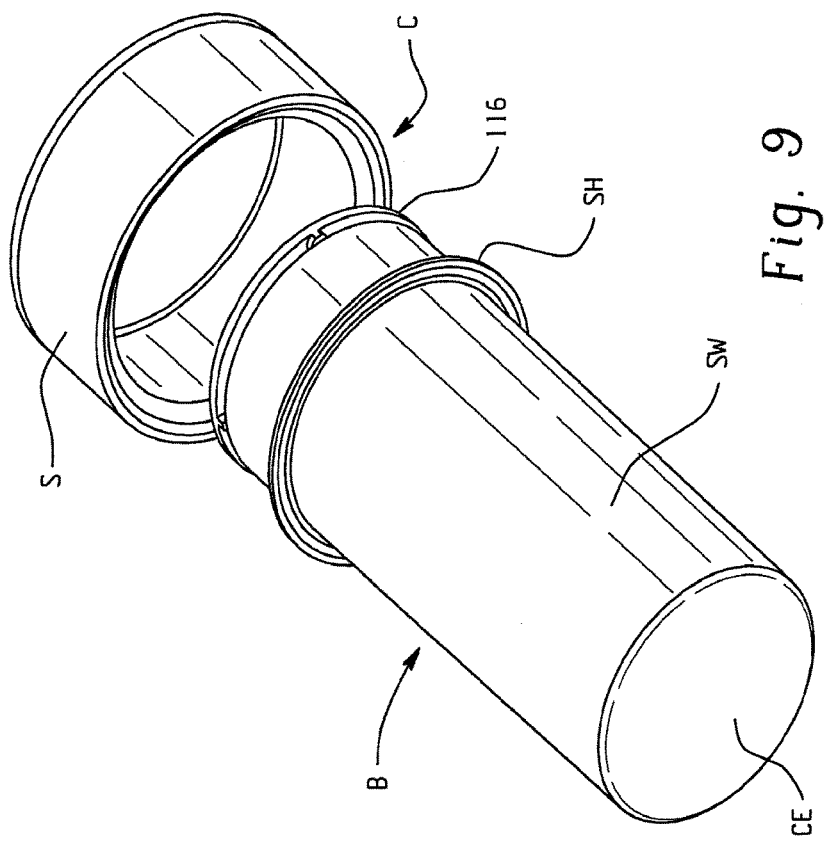
Figure 12:
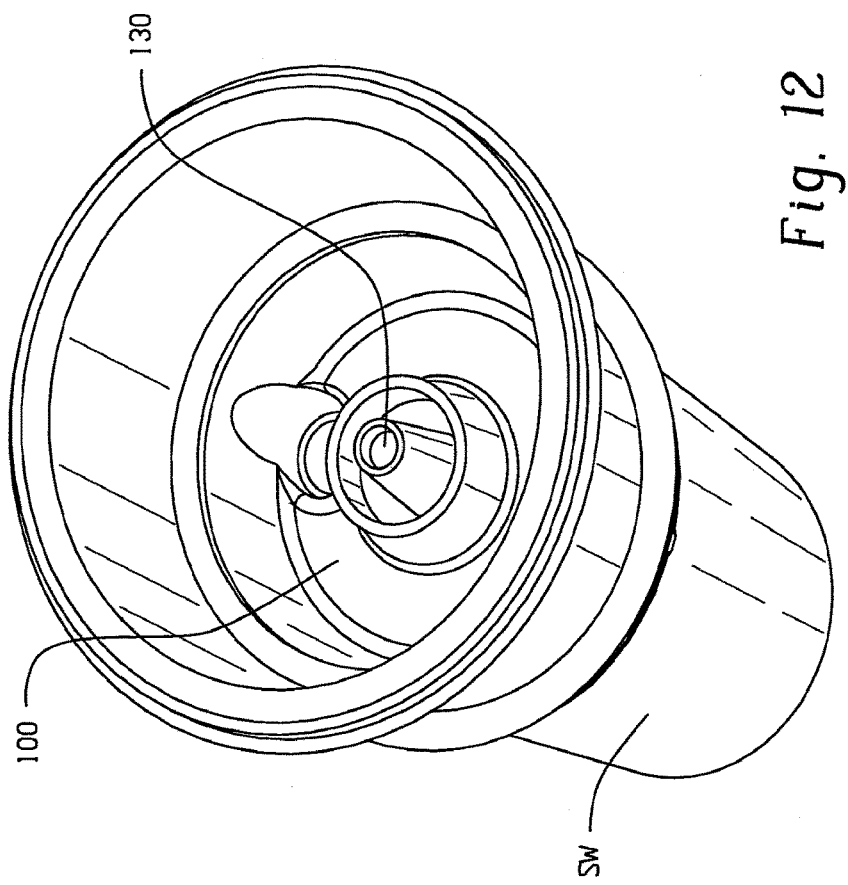
Figure 11:
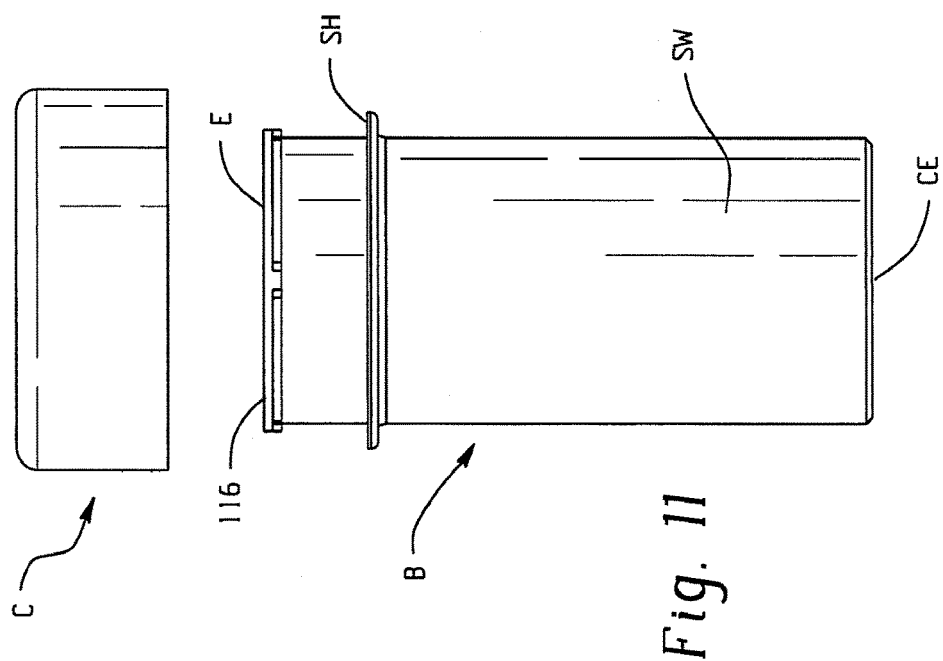

There are certain industries, such as food products, medical, dental, pharmaceutical, laboratories, or in connection with E-cigarettes as described in the Background, where a fluid is contained in the container B. To prevent inadvertent spilling of the fluid contents when the cap C is removed from the container B, an insert is provided in the open end E of the container. A syringe type opening is often used in known inserts, sometimes referred to as vial caps, to receive either a needle or neck of the syringe. The needle may be secured to a conventional syringe SYR (FIG. 2) and is inserted through the insert so that upon application of a vacuum or suction caused by retracting a plunger of the syringe, at least some of the contents of the container can be withdrawn through the needle/neck of the syringe and into a main cavity of the syringe. A vent may also be provided through the insert to permit air to enter the container, and the vent is small enough to prevent leakage or spilling of the container contents.

The present disclosure is directed to a new insert 100 (FIG. 3-17) and combination of the new insert, container B and cap C. It is particularly advantageous if the insert 100 can be used with existing containers B and caps C, but if modifications are required to accommodate the insert 100 then there are still substantial benefits offered by the insert itself. The insert 100 can be formed from a wide variety of materials, although as noted above, a molded plastic construction such as polypropylene is desirable because the insert and container can be used for a wide variety of end uses, made of recycled materials, and easily manufactured, i.e. molded.

In an exemplary embodiment, the insert 100 includes a body 110 having a first or inner end 112 and a second or outer end 114 spaced apart along a first axis. Because the container B oftentimes has a cylindrical cavity, the outer contour of the insert body 110 is likewise substantially cylindrical for sliding, sealing receipt within the sidewall S of the container FIGS. 4, 7, and 8). The insert must be able to essentially contain or seal the material in the container B, or the container or insert 100 be modified to receive a seal member that seals between the container and the insert. The first end 112 of the insert body 110 is thus located inwardly from the opening E of the container B. The outer, second end 114 of the insert body 110 includes a shoulder 116 that extends radially outward from the remainder of the body. The shoulder 116 may be circumferentially continuous or may be discontinuous. In either event, the shoulder 116 is dimensioned to extend radially over the open, second end of the container B so that continued axial advancement of the body 110 into the container is precluded. Likewise, the shoulder 116 preferably has a limited axial dimension so that when inserted in the container B, it does not adversely impact on the threaded receipt of the cap C on to the container. It will also be appreciated that the insert body 110 is dimensioned for a tight, fluid sealing engagement with the inner surface of the sidewall SW of the bottle B and/or the seal member such as an annular O-ring 115 received in a recess formed in a perimeter of the insert adjacent the first, inner thereof. Thus the fluid contents in the container, either introduced before or after the insert is mounted in the open end E of the container, are generally retained by the container.

A passage 130 is provided through the insert 100 and extends entirely through from the first end to the second end of the insert. The passage 130 can be dimensioned to receive a connector, needle, or Luer-type fitting 140 therein. This is similar to known structures so that the size of the passage 130 is made to accommodate either a narrow needle or a larger Luer-type fitting 140 if so desired. The needle or fitting can be connected for communication with the opening 130 in the insert via friction fit or by a threaded engagement such as by adding internal threads to the insert around the opening. Contents of the container B can be removed by inserting/securing the needle/fitting 140 (attached to one end of the syringe SYR) to the insert passage 130. Desirably, a plunger PL is either fully or partially depressed in the syringe SYR so that when the needle/fitting 140 is attached to passage 130, and the syringe plunger withdrawn away from the container B, the contents of the container pass from the container cavity and through the needle/fitting 140, through passage 130 through the insert body, and into the syringe. The fluid contents now held in the syringe SYR are then dispensed into or for a desired end use, e.g., medicinal, e-cigarette, etc. by depressing the plunger PL and forcing the fluid through the needle/fitting 140.

It is often desired to remove the needle/fitting 140 from the syringe SYR. Removing the needle/fitting 140 prevents inadvertent needle sticks, and also reduces the storage length of the syringe SYR. However, in some instances the needle/fitting 140 can be reused and there is a desire to retain the needle/fitting for future use. Heretofore there has been no convenient way to store the needle/fitting 140 during non-use.

The insert body 110 also includes an elongated, axially extending recess 150 that proceeds from the second end 114 of the insert 100 toward the first end 112 and terminates within the body, or a portion of the body such as an extension 160 (FIG. 3) that extends outwardly from a remainder of the first end of the insert body. Described another way, the extension 160 is an elongated hollow structure that is accessible (i.e., has an access opening) from the second end 114 of the insert 100. The recess 150 is dimensioned to receive the needle/fitting 140 when it is removed from the syringe SYR (FIG. 6), and it will be appreciated that the showing of FIG. 6 only illustrates partial insertion of the needle/fitting 140 into the recess 150. The recess 150 serves as a storage compartment for the needle/fitting 140 when the needle/fitting is not being used to withdraw fluid contents from the container B. Thus, when the insert 100 is mounted in the container B, and the cap C is removed from the container, the recess 150 is accessible from the second end of the container. As is also apparent in the Figures, the extension 160 is preferably located between the centrally located passage 130 of the insert 100 and the outer wall that defines the body 110, i.e., at a position offset from the passage. Of course other locations of the passage 130 or recess 150/extension 160 could potentially be used without departing from the scope and intent of the present disclosure. Likewise, the conformation of the recess 150, extension 160, or possibly the perimeter shape of the body 110 may vary without departing from the present disclosure.

Once the needle/fitting 140 is stored in the recess 150/extension 160, the cap C can be threaded onto the container B, and the contents of the container are protected from the outside environment, and likewise the needle/fitting is also protected. By simply removing the cap C from the container B, the stored needle/fitting 140 can be easily accessed, for mounting onto the end of the syringe SYR. It is also contemplated that the needle/fitting 140 can be mounted to the syringe SYR without having to handle the needle/fitting but simply by manipulating the syringe relative to the stored location of the needle/fitting in the recess until the needle/fitting is connected to the syringe and removed from the recess.

Again, this insert 100 and modified container B using this insert can find a wide array of uses including use as a medical device where a blunt needle or pointed needle can be inserted into the recess 150/extension 160, and then the cap C can be screwed on the container which houses the needle/fitting 140 according to the EPA SHARPS rules for disposal.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An insert for use with an associated container that has an end wall and sidewall that together form an internal cavity and an opening opposite the end wall that communicates with the internal cavity, the insert comprising:
   a body having first and second ends spaced apart along a first axis, a portion of the body dimensioned for receipt in the opening of the associated container, wherein the body has a shoulder adjacent the second end that is dimensioned to preclude receipt in the opening of the associated container;
   a passage extending through the body from the first end to the second end for communicating with the internal cavity of the associated container; and
   an elongated recess extending inwardly from the first end of the body and sealed from the cavity of the associated container, wherein the elongated recess has a length measured along the first axis that is dimensioned to receive a needle therein, the recess having an access opening that extends into the body in a direction along the first axis from the second end and beyond the first end of the body whereby the recess extends axially from the first end of the body.

2. The insert of claim 1 wherein the recess projects in a direction substantially parallel with the first axis from the second end of the body and the recess is dimensioned to extend into the cavity of the associated container.

3. The insert of claim 1 wherein the passage in the body is sized to mate with a neck of a syringe.

4. The insert of claim 1 wherein the body terminates in a shoulder at the second end of the body.

5. The insert of claim 1 wherein the recess is a closed bore.

6. The insert of claim 1 wherein the passage is generally centrally located in the body.

7. The insert of claim 1 wherein the recess is offset from the passage.

8. The insert of claim 1 wherein the recess and the passage extend in substantially parallel relation.

9. The insert of claim 1 wherein the body has a substantially cylindrical outer circumferential wall dimensioned for sliding, sealing receipt within the opening of the associated container.

10. The insert of claim 1 wherein the body has a substantially cylindrical outer circumferential wall that is dimensioned for sliding, sealing receipt within the opening of the associated container, and a shoulder having a dimension that precludes insertion of the shoulder into the opening of the associated container.

11. The insert of claim 10 wherein the shoulder has a reduced dimension measured along the first axis and forms a lip that abuttingly engages an outer end of the associated container around the opening and prevents further insertion of the body into the associated container.

12. The insert of claim 11 wherein the shoulder is substantially circumferentially continuous for engaging an end of the associated container around the opening.

13. The insert of claim 1 wherein the insert is a molded plastic.

14. The insert of claim 1 wherein the insert is a molded polypropylene.

15. The insert of claim 1 wherein the body is one-piece.

16. The container assembly of claim 1 wherein a first end of the recess has an access opening at the insert body first end, and a second end of the recess is axially spaced from the recess first end and is closed.

17. A container assembly comprising:
a container having an end wall, a sidewall having a first end extending from the end wall whereby the end wall and sidewall together form an internal cavity, and an opening at a second end of the sidewall opposite the end wall that communicates with the internal cavity;
a cap selectively received at the second end of the sidewall and dimensioned for closing receipt with the opening; and
an insert including a body having first and second ends spaced apart along a first axis, a portion of the body dimensioned for receipt in the opening of the container, a passage extending through the body from the insert body first end to the insert body second end for communicating with the internal cavity of the container, and an elongated recess extending inwardly from the first end of the body and always sealed from the cavity of the container, wherein the recess has an access opening that extends into the body in a direction along the first axis from the second end and the recess extends axially from the first end of the body.

18. The container of claim 17 wherein the cap and the container include cooperating thread lugs for selective threaded receipt of the cap on the container.

19. The container of claim 18 wherein the cap and the container are molded plastic.

20. The container of claim 18 wherein the body has a substantially cylindrical outer circumferential wall that is dimensioned for sliding, sealing receipt within the opening of the container, and a shoulder having a dimension that precludes insertion of the shoulder into the opening of the container.

21. The container of claim 20 wherein the shoulder has a reduced dimension measured along the first axis and forms a lip that abuttingly engages an outer end of the container around the opening and prevents further insertion of the insert into the container.

22. The container of claim 21 wherein the cap and the container include cooperating thread lugs for selective threaded receipt of the cap on the container, and the cooperating thread lugs accommodate the shoulder of the insert when the insert is mounted in the container and the cap is received on the container.

23. The container assembly of claim 17 wherein the recess projects in a direction substantially parallel with the first axis from second end of the body and the recess is dimensioned to extend into the cavity of the container.

24. The container assembly of claim 17 wherein the passage in the body has an outer end sized to mate with a neck of a syringe.

25. The container assembly of claim 17 wherein the elongated recess has a length measured along the first axis that is dimensioned to receive a needle therein.

26. The container assembly of claim 17 wherein the body has a shoulder adjacent the second end that is dimensioned to preclude receipt in the opening of the container.

27. The container assembly of claim 17 wherein the body terminates in a shoulder that is located at the second end of the body.

28. The container assembly of claim 17 wherein the recess is a closed bore.

29. The container assembly of claim 17 wherein the passage is generally centrally located in the body.

30. The container assembly of claim 17 wherein the recess is offset from the passage.

31. The container assembly of claim 17 wherein the recess and the passage extend in substantially parallel relation.

32. The container assembly of claim 17 wherein the body has a substantially cylindrical outer circumferential wall that is dimensioned for sliding, sealing receipt within the opening of the container.

33. The container assembly of claim 17 wherein the body has a substantially cylindrical outer circumferential wall that is dimensioned for sliding, sealing receipt within the opening of the associated container, and a shoulder having a dimension that precludes insertion of the shoulder into the opening of the container.

34. The container assembly of claim 33 wherein the shoulder has a reduced dimension measured along the first axis and forms a lip that abuttingly engages an outer end of the container around the opening and prevents further insertion of the insert into the container.

35. The container assembly of claim 34 wherein the shoulder is substantially circumferentially continuous for engaging an end of the container around the opening.

36. The container assembly of claim 17 wherein the insert is a molded plastic.

37. The container assembly of claim 17 wherein the insert is molded.

38. The container assembly of claim 17 wherein the body is one-piece.

39. The container assembly of claim 17 wherein a first end of the recess has an access opening at the insert body first end, and a second end of the recess is axially spaced from the recess first end and is closed.

* * * * *